United States Patent [19]

Breuer et al.

[11] 4,268,224

[45] May 19, 1981

[54] METHOD OF AND MEANS FOR CONVEYING AND MEASURING GASES FOR GAS ANALYSIS OPERATIONS

[75] Inventors: Wolfram Breuer; Klaus Siemer, both of Leverkusen, Fed. Rep. of Germany

[73] Assignee: Farbenfabriken Bayer Aktiengesellschaft, Leverkusen, Fed. Rep. of Germany

[21] Appl. No.: 708,154

[22] Filed: Jul. 23, 1976

Related U.S. Application Data

[63] Continuation of Ser. No. 836,008, Jun. 24, 1969, abandoned, which is a continuation of Ser. No. 251,846, May 5, 1972, abandoned.

[30] Foreign Application Priority Data

Jul. 8, 1969 [DE] Fed. Rep. of Germany ....... 1973796

[51] Int. Cl.³ .................... F04B 49/06; H02P 5/28
[52] U.S. Cl. ...................... 417/32; 318/471; 318/334
[58] Field of Search ................... 318/334, 471; 417/32

[56] References Cited

U.S. PATENT DOCUMENTS

| | | | |
|---|---|---|---|
| 2,424,344 | 7/1947 | Veinott | 318/334 |
| 3,384,801 | 5/1968 | Rodgers | 318/334 |
| 3,475,677 | 10/1969 | Swinehart et al. | 318/471 |
| 3,492,946 | 2/1970 | Martin | 73/422 |
| 3,501,899 | 3/1970 | Allor | 417/32 |
| 3,544,236 | 3/1969 | BRookmire | 417/32 |

*Primary Examiner*—William L. Freeh
*Attorney, Agent, or Firm*—Sprung, Felfe, Horn, Lynch & Kramer

[57] ABSTRACT

This invention relates to a method of and means for conveying and measuring gases for gas analysis operations by means of a pump, which conveys the gas with constant volume per working cycle. The means for this purpose, as used in connection with gas analysis instruments, consists of a cyclically operating gas delivery pump with an electric motor drive which is connected to a frequency transmitter for pre-setting the speed of rotation.

2 Claims, 2 Drawing Figures

METHOD OF AND MEANS FOR CONVEYING AND MEASURING GASES FOR GAS ANALYSIS OPERATIONS

This application is a continuation of application Ser. No. 836,008 filed June 24, 1969 now abandoned, which is a continuation of application Ser. No. 251,846 filed May 5, 1972, now abandoned.

It is known to adjust constant gas flows which are necessary for gas analysis by means of pumps which show a constant delivery volume per working cycle and the driving frequency of which is kept constant. Such a pump supplies a constant volumetric flow which is frequently sufficient for the analysis. In many cases, however, the analysis requires a constant mass flow, more especially when the analysis result has to be related to the defined and constant gas state, e.g. to cubic meters at n.t.p. In such cases, when using a pump of constant volumetric flow, the variation in the operative values of pressure and temperature of the gas to be investigated enter as error deviation into the analysis result. Already with investigations of air, the metereologically established changes in condition of the air, for example, in the settled area of North West Germany, lead to an error of ±7.5% (92.5% reliability). On the other hand, after taking into account the temperature, there still remains a residual error of ±2.2% (97.8% reliability), on account of the uncorrected fluctuations in pressure.

Such regard to the temperature, which increases the accuracy of gas analyses, has so far usually been effected by a costly thermostatic control of the system or by evaluating the separately measured temperatures by calculation.

It has now been found that the disadvantages can be avoided and the measurement result can be improved by the time sequence of the operating cycles of the pump being altered by the gas temperature in the sense of a delivery of constant mass. In this way, the temperature errors are avoided which gave an incorrect measurement result with the prior known methods.

According to the invention, the means for carrying the method into effect are characterised in that a temperature sensing device is arranged in the gas delivery pump, said device being coupled to the frequency transmitter for altering the timing of the gas delivery pump in the sense of a gas delivery of constant mass.

The invention is to be explained by reference to one constructional example and a drawing, wherein.

Figure 1:
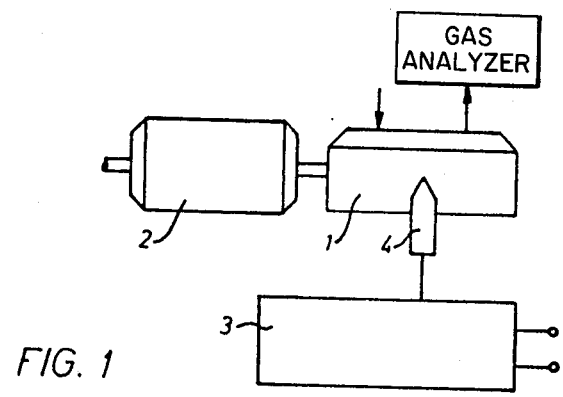
FIG. 1 shows the means as a block diagram.

In FIG. 1, a pump 1 of constant delivery volume per working cycle is driven by an electric motor 2, the speed of which is pre-set by the frequency of a frequency transmitter 3. The frequency transmitter 3 is controlled by a temperature sensing device 4 arranged in the pump 1 on the suction side so that the sequence of the working cycles of the pump 1 is altered in the sense of a gas delivery of constant mass. By way of example, a rise in the gas temperature causes an increase in frequency, which is balanced so that exactly just as much more volume is delivered as the mass per volume has decreased because of the rise in temperature. A correspondingly opposite effect occurs when the gas temperature falls.

This means for conveying and measuring a gas has the great advantage that the gas delivery pump according to the invention, necessary in any case for gas analysis, is only to be slightly modified in order to deliver the required constant mass, more especially since usually the gas quantities required for the analysis operations are conveyed with low-power units and in many cases analysis operations which are independent of the mains are carried out with battery-operated pumps, which are already driven by synchronous motors with electronic frequency transmitters.

Figure 2:
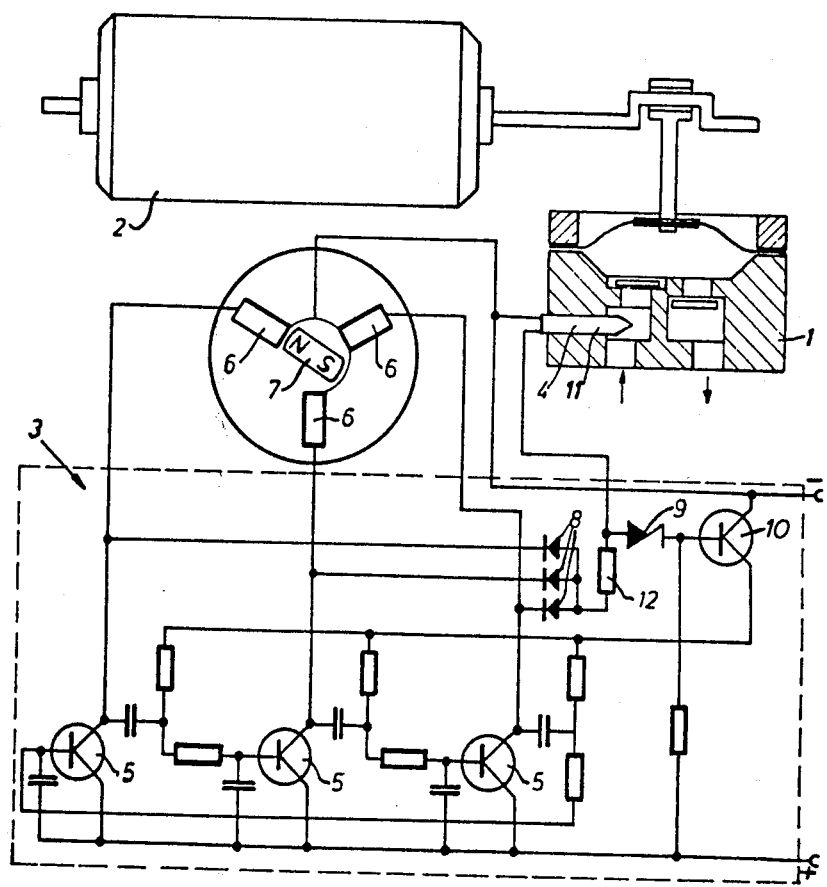
FIG. 2 shows the technical embodiment of the said means.

In FIG. 2, a closed circuit arrangement with three transistors 5 is so arranged that in each case one of these transistors 5 is electrically conducting, makes the following conducting and then itself becomes non-conducting, The three direct current pulses shifted in phase in each case by 120° produce a rotational field in the three field windings 6 of the electric motor 2, the magnet armature of the motor 2 rotating with the frequency of said field. The inverse voltages induced in the field winding 6 of the motor 2 are proportional to the speed of rotation of the motor 2. They are decoupled by means of three rectifiers 8, smoothed and fed by way of a Zener diode 9 to a control transistor 10. If the induction voltage, because of increased motor speed, exceeds the Zener voltage, the control transistor 10 causes a fall in the frequency in the sense of a constant speed of rotation of the armature 7.

The speed of rotation of the motor 2 can be altered by the induced voltage being connected to a voltage divider, consisting of the resistances 11 and 12, the tapping of said divider being connected to the Zener diode 9. Since a constant resistance 12 and a temperature-dependent resistance 11, simultaneously representing the temperature sensing device 4, have been chosen as voltage divider, the speed of rotation of the motor 2 is variable in the sense of a gas delivery of constant mass, depending on the temperature measured in the gas delivery pump.

We claim:

1. In gas analysis apparatus, wherein a gas stream is delivered to gas analysis means via a pump having a constant volume throughput per working cycle and an electric motor for driving the pump and having a controllable speed of rotation upon which the frequency of the pump is dependent, the improvement comprising:
    (a) measuring means for measuring the pump inlet temperature of said gas stream and
    (b) a frequency transmitter responsive to the measuring means to vary the frequency thereof as a function of said temperature, and for controlling the speed of rotation of said electric motor to vary same in response to changes in said temperature and thereby varying the volume delivered by said pump per unit time to compensate for changes in said temperature whereby a constant mass flow per unit time is delivered by the pump to the gas analysis means.

2. Apparatus according to claim 1, said temperature measuring means comprising a temperature dependent resistance element.

* * * * *

UNITED STATES PATENT AND TRADEMARK OFFICE
CERTIFICATE OF CORRECTION

PATENT NO. : 4,268,224
DATED : May 19, 1981
INVENTOR(S) : Wolfram Breuer et al

It is certified that error appears in the above-identified patent and that said Letters Patent are hereby corrected as shown below:

Title Page    Delete "1969" and insert --1968--.
Priority      Delete "1973796." and insert --1773796--.

Signed and Sealed this

Fourth Day of September 1984

[SEAL]

Attest:

GERALD J. MOSSINGHOFF

Attesting Officer     Commissioner of Patents and Trademarks